United States Patent
Lee et al.

(10) Patent No.: US 6,635,229 B1
(45) Date of Patent: Oct. 21, 2003

(54) METHOD FOR LOW PERFLUOROCARBON COMPOUND EMISSION

(75) Inventors: Wei W. Lee, Plano, TX (US); Albert H-B Cheng, Richardson, TX (US); Qizhi He, Plano, TX (US)

(73) Assignee: Texas Instruments Incorporated, Dallas, TX (US)

(*) Notice: Subject to any disclaimer, the term of this patent is extended or adjusted under 35 U.S.C. 154(b) by 304 days.

(21) Appl. No.: 09/642,199

(22) Filed: Aug. 18, 2000

Related U.S. Application Data

(60) Provisional application No. 60/154,928, filed on Sep. 21, 1999.

(51) Int. Cl.⁷ .................................................. C01B 7/24
(52) U.S. Cl. .................................................. 423/240 R
(58) Field of Search .................... 423/240 R, 245.2, 423/245.1, 462, 644; 588/212, 213, 210, 248, 205; 427/255.39

(56) References Cited

U.S. PATENT DOCUMENTS

| | | | | |
|---|---|---|---|---|
| 5,416,247 A | * | 5/1995 | Webster | 588/206 |
| 5,547,653 A | * | 8/1996 | Webster et al. | 423/445 R |
| 5,559,278 A | * | 9/1996 | Mouk et al. | 588/205 |
| 5,602,295 A | * | 2/1997 | Abel et al. | 588/205 |
| 5,852,148 A | * | 12/1998 | Behr et al. | 526/245 |

* cited by examiner

*Primary Examiner*—Stanley S. Silverman
*Assistant Examiner*—Edward M. Johnson
(74) *Attorney, Agent, or Firm*—Wade James Brady III; Frederick J. Telecky, Jr.

(57) ABSTRACT

A method of reducing perfluorocarbon emissions wherein a plasma reactor or thermal chamber is provided and a gaseous single halogen-containing perfluorocarbon is entered into the reactor or thermal chamber. The perfluorocarbon is altered in the plasma reactor or thermal chamber to one of a bromine-containing and/or iodine-containing carbon species and expelled from the reactor or thermal chamber. The alteration includes entering into the plasma reactor or thermal chamber a species taken from the class consisting of iodine, bromine, hydrogen iodide, hydrogen bromide, bromocarbon compound and iodocarbon compounds. When the reactor is a thermal chamber, the temperature in the thermal chamber is at least 800° C. and the single halogen-containing species is located in the chamber for from about 1 minute to about 3 minutes. When the reactor is a plasma reactor, a plasma is provided in the plasma reactor to dissociate all of the halogen-containing species in the reactor with the dissociated species combining to form more energetically favorable species which are more environmentally friendly.

16 Claims, 1 Drawing Sheet

METHOD FOR LOW PERFLUOROCARBON COMPOUND EMISSION

This application claims priority under 35 USC 119(e)(1) of provisional application No. 60/154,928 filed Sep. 21, 1999.

BACKGROUND OF THE INVENTION

1. Field of the Invention

This invention relates to a method for reducing and possibly eliminating perfluorocarbon compounds (PFCs) gaseous emissions which produce global warming during fabrication of devices in the semiconductor and other industries.

2. Brief Description of the Prior Art

Due to the green house effect, there has been an industrywide commitment to reduce and possibly eliminate the causes of the green house effect. One such cause is emission into the atmosphere of perfluoro compounds also know as PFCs. The perfluorocarbons, such as but not limited to $CF_4$, $CHF_3$, $C_2F_6$, $C_3F_8$, $SF_6$ and $NF_3$, are known to have very high global warming potentials and governmental agencies have been and continue to seek ways to reduce the emissions of these compounds. Abatement techniques for perfluorocarbon emissions using heat or plasma are presently commercially available, however, most of the byproducts are still providing high global warming potentials as well as hazardous air pollutants and are relatively costly.

In the prior art, the gaseous effluent of procedures utilizing perfluoro compounds has generally been exhausted into the atmosphere, this being attributed as a cause of the green house effect or, alternatively, the use of fluorine-containing compounds has been restricted, either voluntarily or involuntarily, generally by substitution therefore of other materials. While this procedure is helpful, often the substituted materials provide inferior results as compared with the discarded fluorine-containing material which it replaced.

While thermal and plasma abatement units are presently available for use in the manufacture of semiconductors for removal of perfluorocarbon species, as stated above, the cost of such units and the unwanted byproducts developed by these units are still a material concern in the industry, especially by-products such as HF, which is a hazardous air pollutant, still regulated by the EPA. It is therefore apparent that improved procedures are required.

SUMMARY OF THE INVENTION

In accordance with the present invention, a method is provided for minimizing if not eliminating emissions of perfluorocompounds while retaining the use of such materials in a fabrication process by providing chemical trapping techniques to produce environmentally benign species, both by thermal and plasma source in a relatively inexpensive manner.

In the semiconductor industry, PFCs are used in the fabrication of semiconductor devices in both plasma etching and chamber cleaning sources after chemical vapor deposition (CVD) processes. No alternative fluorine sources have been found to replace the prior art PFC compounds with better or equivalent efficiency. The destruction efficiency for these compounds under a plasma reactor is low (from about 20 to about 30 percent) due to the recombination of the highly stable compounds, such as $CF_4$.

Briefly, the above is accomplished by chemically trapping perfluorocarbon species by either plasma or thermal sources. A plasma or thermal source is provided at a downstream chamber in the fabrication process to break down the PFC emissions into highly reactive free radicals or ions along with trapping reagents, such as, but not limited to, iodine ($I_2$), hydrogen iodide (HI), $CH_3I$, $C_2H_5I$, $CH_3Br$, bromine ($Br_2$), $C_2H_5Br$, hydrogen bromide (HBr). The iodo and bromo carbon compounds are formed prior to the $CF_4$ at a high energy stage, 800° C. or higher, and before emission of the $CF_4$ to the atmosphere. These high energy iodo and/or bromo compounds are reacted with the $CF_3$ species prior to emitting to the atmosphere to produce by-products such as, but not limited to, and of the type $CF_3I$, $CF_3Br$. These iodo and bromo compounds have from about one tenth to about one one hundredth less global warming potential than do standard PFCs and can be treated as environmentally benign products.

The mechanism upon which the above described reactions take place whereby the perfluorocarbons are converted to iodoperfluoro and bromoperfluoro carbons is based upon the bond dissociation energies which are favorable to such conversion.

In accordance with a first embodiment of the present invention, a gas inlet receives a perfluorocarbon. The perfluorocarbon, along with possibly other reagents, is passed into a PECVD or plasma etch reactor wherein a processing step is effected with the effluent from the processing step still containing a perfluorocarbon. The effluent from the reactor is passed to a thermal chamber wherein the effluent containing the perfluorocarbon is mixed at a temperature greater than 800° C. for a period of from about 1 to about 3 minutes with bromine-containing and/or iodine-containing compounds and/or bromine and/or iodine. The perfluorocarbon compound is reacted in the thermal chamber with the non-fluorine-containing halogen and/or halogen-containing compound to form halocarbons which contain iodine and/or bromine in addition to or without fluorine within the thermal chamber. Little or no perfluorocarbons containing which are otherwise halogen-free remain in the effluent from the chamber.

In accordance with a second embodiment of the present invention a gas inlet receives a perfluorocarbon. The perfluorocarbon, along with possibly other reagents, is passed into a PECVD or plasma etch reactor wherein a processing step is effected with the effluent from the processing step still containing a perfluorocarbon. The effluent from the reactor is passed to a plasma reactor wherein the effluent containing the perfluorocarbon is reacted with a plasma which is a bromine-containing and/or iodine-containing compound and/or bromine and/or iodine. All species will be dissociated by either plasma or heat and recombined to form energetically favorable non or less global warming species, whether non-fluorine or fluorohalogen, which will then be emitted to the atmosphere. The perfluorocarbon compound is reacted in the plasma reactor with the non-fluorine-containing halogen and/or halogen-containing compound to form halocarbons which contain iodine and/or bromine in addition to or without fluorine within the plasma reactor. Little or no perfluorocarbons containing no other halogen remain in the effluent from the reactor.

DESCRIPTION OF THE PREFERRED EMBODIMENTS

Figure 1:
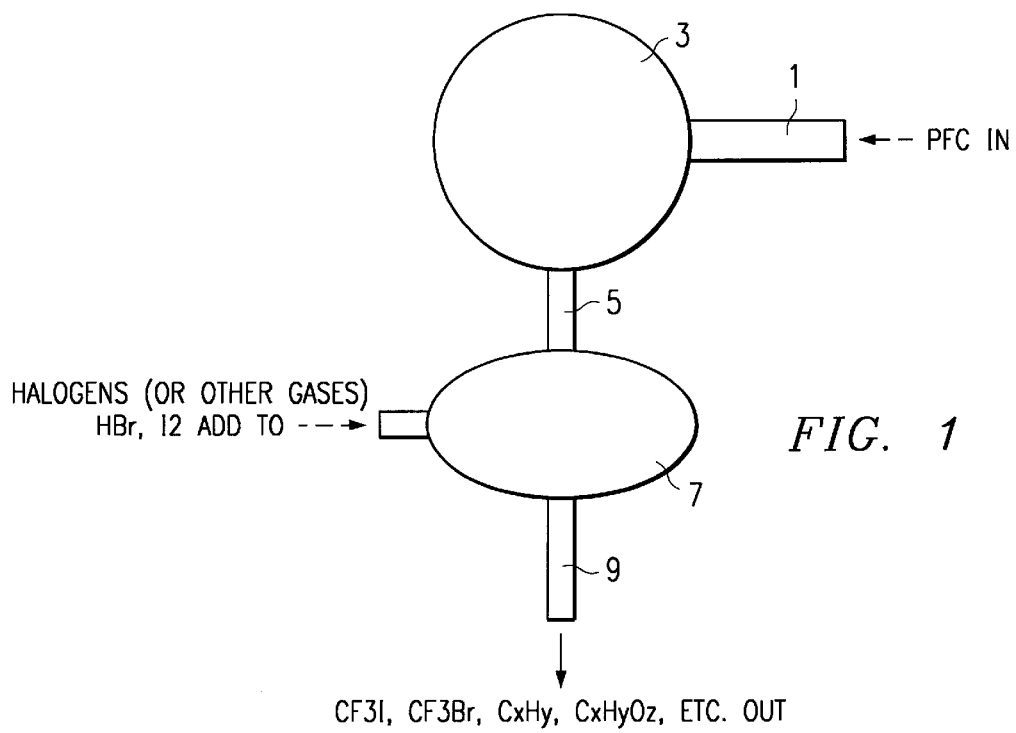
FIG. 1 is a schematic diagram in accordance with a first embodiment of the present invention.

Referring first to FIG. 1, there is shown a method in accordance with a first embodiment of the present invention. There is shown a gas inlet 1 which receives a perfluorocarbon such as, for example, $CF_4$. The fluorocarbon, along with possibly other reagents, is passed into a PECVD or plasma etch reactor 3 wherein a deposition or etch processing step will be effected with the effluent from a processing step still contain a perfluorocarbon. The effluent from the reactor 3 is passed along a pipe 5 to a thermal chamber 7 wherein the effluent containing the perfluorocarbon is mixed at a temperature of at least 800° C. for a period of from about 1 to about 3 with bromine-containing and/or iodine-containing compounds and/or bromine and/or iodine. The perfluorocarbon compound is reacted in the thermal or plasma chamber 7 with the non-fluorine-containing halogen and/or halogen-containing compound to form halocarbons which contain iodine and/or bromine in addition to or without fluorine within the thermal chamber. Little or no perfluorocarbons containing other halogen remain in the effluent from the chamber 7 which now travels to the atmosphere or other location through the outlet 9.

Figure 2:
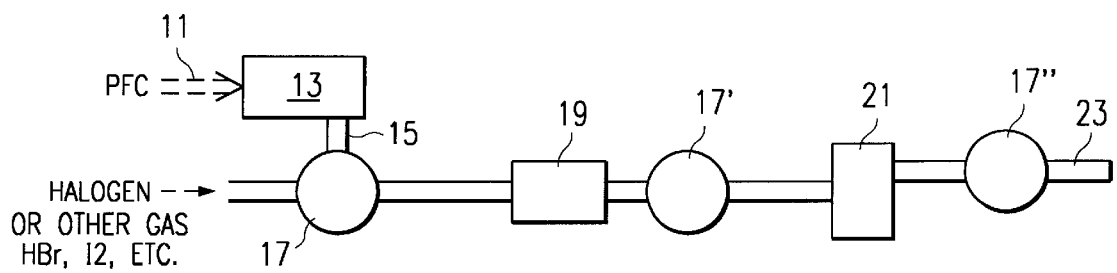
FIG. 2 is a schematic diagram in accordance with a second embodiment of the present invention.

Referring to FIG. 2, there is shown a method in accordance with a second embodiment of the present invention. There is shown a gas inlet 11 which receives a perfluorocarbon such as, for example, $CF_4$. The perfluorocarbon, along with possibly other reagents, is passed into a PECVD or plasma etch reactor 13 wherein a deposition or etch processing step will be effected with the effluent from a processing step still contain a perfluorocarbon. The effluent from the reactor 13 is passed along a pipe 15 to a plasma reactor 17 wherein the effluent containing the perfluorocarbon is reacted with a plasma which is a bromine-containing and/or iodine-containing compound and/or bromine and/or iodine. The perfluorocarbon compound is reacted in the plasma reactor 17 with the non-fluorine-containing halogen and/or halogen-containing compound to form halocarbons which contain iodine and/or bromine in addition to or without fluorine within the plasma reactor. Little or no perfluorocarbons containing no other halogen remain in the effluent from the reactor 17 which now travels to the atmosphere or other location through via a pump 19 and a scrubber 21 to the outlet 23. While the plasma reactor 17 is shown disposed upstream of the pump 19, it can also be disposed as shown between the pump and the scrubber at 17' or between the scrubber and the outlet at 17".

Though the invention has been described with reference to specific preferred embodiments thereof, many variations and modifications will immediately become apparent to those skilled in the art. It is therefore the intention that the appended claims be interpreted as broadly as possible in view of the prior art to include all such variations and modifications.

What is claimed is:

1. A method of reducing perfluorocarbon emissions in a semiconductor fabrication process which includes the steps of:
    (a) providing one of a plasma reactor or thermal chamber downstream from the use of said perfluorocarbon in said semiconductor fabrication process;
    (b) entering a gaseous perfluorocarbon into said plasma reactor or thermal chamber;
    (c) altering said perfluorocarbon in said plasma reactor or thermal chamber to a species selected from the group consisting of bromine-containing and iodine-containing carbon species; and
    (d) expelling said altered perfluorocarbon from said plasma reactor or thermal chamber.

2. The method of claim 1 wherein said step of altering comprises the step of entering into said plasma reactor or thermal chamber a species taken from the class consisting of iodine, bromine, hydrogen iodide, hydrogen bromide, bromocarbon compounds and iodocarbon compounds.

3. The method of claim 2 wherein said step of altering is in a thermal chamber, the temperature in said thermal chamber being at least about 800° C. and said halogen-containing species being located in said thermal chamber for from about 1 minute to about 3 minutes.

4. The method of claim 3 wherein said step of altering is in a plasma reactor and wherein a plasma is provided in said plasma reactor to dissociate said halogen-containing species in said plasma reactor and cause the dissociated halogen-containing species to combine in said plasma reactor with at least one of a bromine-containing or iodine-containing carbon species to form more energetically favorable species which are more environmentally friendly than said gaseous perfluorocarbon.

5. The method of claim 2 wherein said step of altering is in a plasma reactor and wherein a plasma is provided in said plasma reactor to dissociate said halogen-containing species in said plasma reactor and cause the dissociated halogen-containing species to combine in said plasma reactor with at least one of a bromine-containing or iodine-containing carbon species to form more energetically favorable species which are more environmentally friendly than said gaseous perfluorocarbon.

6. The method of claim 1 wherein said step of altering is in a thermal chamber, the temperature in said thermal chamber being at least about 800° C. and said halogen-containing species being located in said thermal chamber for from about 1 minute to about 3 minutes.

7. The method of claim 6 wherein said step of altering is in a plasma reactor and wherein a plasma is provided in said plasma reactor to dissociate said halogen-containing species in said plasma reactor and cause the dissociated halogen-containing species to combine in said plasma reactor with at least one of a bromine-containing or iodine-containing carbon species to form more energetically favorable species which are more environmentally friendly than said gaseous perfluorocarbon.

8. The method of claim 1 wherein said step of altering is in a plasma reactor and wherein a plasma is provided in said plasma reactor to dissociate said halogen-containing species in said plasma reactor and cause the dissociated halogen-containing species to combine in said plasma reactor with at least one of a bromine-containing or iodine-containing carbon species to form more energetically favorable species which are more environmentally friendly than said gaseous perfluorocarbon.

9. A method of reducing perfluorocarbon emissions in a semiconductor fabrication process which includes the steps of:
    (a) providing one of a plasma reactor or thermal chamber downstream from the use of said perfluorocarbon in said semiconductor fabrication process;
    (b) entering a gaseous perfluorocarbon into said plasma reactor or thermal chamber and causing said gaseous perfluorocarbon to break down in said plasma reactor thermal chamber to provide highly reactive free radicals;
    (c) altering said perfluorocarbon in said plasma reactor or thermal chamber to a species selected from the group consisting of bromine-containing and iodine-containing carbon species by the entry of a trapping agent into said plasma reactor or thermal chamber concurrently with said break down of said gaseous perfluorocarbon with a species selected from the group consisting of bromine-containing and iodine-containing species; and (d) expelling said altered perfluorocarbon from said plasma reactor or thermal chamber.

10. The method of claim 9 wherein said step of altering comprises the step of entering into said plasma reactor or thermal chamber a species taken from the class consisting of iodine, bromine, hydrogen iodide, hydrogen bromide, bromocarbon compounds and iodocarbon compounds.

11. The method of claim 10 wherein said step of altering is in a thermal chamber, the temperature in said thermal chamber being at least about 800° C. and said halogen-containing species being located in said thermal chamber for from about 1 minute to about 3 minutes.

12. The method of claim 11 wherein said step of altering is in a plasma reactor and wherein a plasma is provided in said plasma reactor to dissociate said halogen-containing species in said plasma reactor and cause the dissociated halogen-containing species to combine in said plasma reactor with at least one of a bromine-containing or iodine-containing carbon species to form more energetically favorable species which are more environmentally friendly than said gaseous perfluorocarbon.

13. The method of claim 10 wherein said step of altering is in a plasma reactor and wherein a plasma is provided in said plasma reactor to dissociate said halogen-containing species in said plasma reactor and cause the dissociated halogen-containing species to combine in said plasma reactor with at least one of a bromine-containing or iodine-containing carbon species to form more energetically favorable species which are more environmentally friendly than said gaseous perfluorocarbon.

14. The method of claim 9 wherein said step of altering is in a thermal chamber, the temperature in said thermal chamber being at least about 800° C. and said halogen-containing species being located in said thermal chamber for from about 1 minute to about 3 minutes.

15. The method of claim 14 wherein said step of altering is in a plasma reactor and wherein a plasma is provided in said plasma reactor to dissociate said halogen-containing species in said plasma reactor and cause the dissociated halogen-containing species to combine in said plasma reactor with at least one of a bromine-containing or iodine-containing carbon species to form more energetically favorable species which are more environmentally friendly than said gaseous perfluorocarbon.

16. The method of claim 9 wherein said step of altering is in a plasma reactor and wherein a plasma is provided in said plasma reactor to dissociate said halogen-containing species in said plasma reactor and cause the dissociated halogen-containing species to combine in said plasma reactor with at least one of a bromine-containing or iodine-containing carbon species to form more energetically favorable species which are more environmentally friendly than said gaseous perfluorocarbon.

* * * * *